US00PP35709P2

(12) United States Plant Patent
Spil

(10) Patent No.: US PP35,709 P2
(45) Date of Patent: Mar. 26, 2024

(54) ***ECHINACEA* PLANT NAMED 'IFECSSSWFU'**

(50) Latin Name: *Echinacea hybrida*
Varietal Denomination: IFECSSSWFU

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/114,823

(22) Filed: Feb. 27, 2023

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS

PP18,429 P2 * 1/2008 Oudolf ..... A01H 5/02 Plt./428

OTHER PUBLICATIONS

CPVO Register S2/S3 version 4.9.9, retrieved on Jun. 14, 2023 at https://online.plantvarieties.eu/publicSearch?denomination=ifecssswfu, 2 pp. (Year: 2023).*
Ditoplant Export BV retrieved on Jun. 20, 2023 at https://www.ditoplant.nl/?p=pagina&s=30&lang=en, pp. 1,8. (Year: 2023).*
Floraxchange retrieved on Jun. 20, 2023 at https://www.floraxchange.nl/Artikel/Info/1175104/Echinacea-Sunseekers-Sweet-Fuchsia, one page. (Year: 2023).*

* cited by examiner

*Primary Examiner* — June Hwu
(74) *Attorney, Agent, or Firm* — C. Anne Whealy

(57) ABSTRACT

A new and distinct cultivar of *Echinacea* plant named 'IFECSSSWFU', characterized by its relatively compact and broadly upright plant habit; moderately vigorous to vigorous growth habit; freely branching habit; strong flowering stems; numerous semi-double type inflorescences with purplish red-colored ray florets and dark red-colored receptacle spines; and good garden performance.

2 Drawing Sheets

Figure 1:
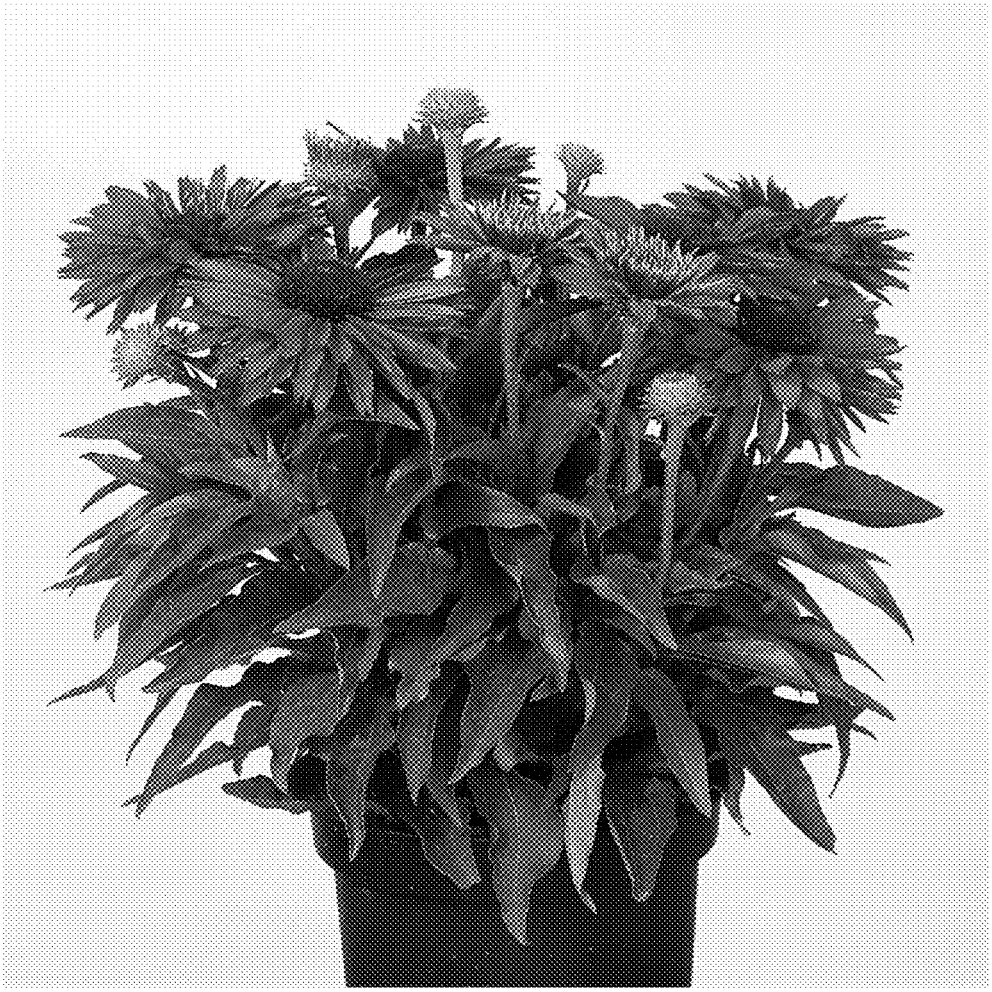

Botanical designation: *Echinacea hybrida.*
Cultivar denomination: 'IFECSSSWFU'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 24, 2022, application number 2022/2659. Foreign priority is not claimed to this application.

BACKGROUND OF THE INVENTION

The present invention relates to a new and distinct cultivar of *Echinacea* plant, botanically known as *Echinacea hybrida*, and hereinafter referred to by the name 'IFECSSSWFU'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from a cross-pollination by the Inventor in July, 2019 in Heerhugowaard, The Netherlands of a proprietary selection of *Echinacea hybrida* identified as code number 009-15-K009-01, not patented, as the female, or seed, parent with a proprietary selection of *Echinacea hybrida* identified as code number 009-16-K042-02, not patented, as the male, or pollen, parent. The new *Echinacea* plant was discovered and selected by the Inventor as a single flowering plant from within the progeny of the stated cross-pollination grown in a controlled greenhouse environment in Heerhugowaard, The Netherlands in August, 2020.

Asexual reproduction of the new *Echinacea* plant by in vitro meristem culture in a controlled environment in Heerhugowaard, The Netherlands since September, 2020 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSSWFU'. These characteristics in combination distinguish 'IFECSSSWFU' as a new and distinct *Echinacea* plant:

1. Relatively compact and broadly upright plant habit.
2. Moderately vigorous to vigorous growth habit.
3. Freely branching habit.
4. Strong flowering stems.
5. Numerous semi-double type inflorescences with purplish red-colored ray florets and dark red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Plants of the new *Echinacea* have stronger and healthier foliage than plants the female parent selection.
3. Inflorescences of plants of the new *Echinacea* have about four whorls of ray florets whereas inflorescences of plants of the female parent selection have two whorls of ray florets.
4. Ray florets of plants of the new *Echinacea* are purplish red in color whereas ray florets of plants of the female parent selection are pinkish purple in color.

Plants of the new *Echinacea* can be compared to plants of the male parent selection. Plants of the new *Echinacea* differ primarily from plants of the male parent selection in the following characteristics:

1. Plants of the new *Echinacea* are more compact than plants of the male parent selection.
2. Plants of the new *Echinacea* have stronger and healthier foliage than plants the male parent selection.
3. Inflorescences of plants of the new *Echinacea* have about four whorls of ray florets whereas inflorescences of plants of the male parent selection have two whorls of ray florets.

Plants of the new *Echinacea* can be compared to plants of *Echinacea purpurea* 'Fatal Attraction' disclosed in U.S. Plant Pat. No. 18,429. In side-by-side comparisons, plants of the new *Echinacea* differ primarily from plants of 'Fatal Attraction' in the following characteristics:

1. Plants of the new *Echinacea* are more compact than plants of 'Fatal Attraction'.
2. Plants of the new *Echinacea* flower earlier than plants of 'Fatal Attraction'.
3. Inflorescences of plants of the new *Echinacea* have about four whorls of ray florets whereas inflorescences of plants of 'Fatal Attraction' have a single whorl of ray florets.

Plants of the new *Echinacea* can also be compared to plants of *Echinacea purpurea* 'Mistral', disclosed in U.S. Patent Publication number 2009/0271902. In side-by-side comparisons, plants of the new *Echinacea* differ primarily from plants of 'Mistral' in the following characteristics:

1. Plants of the new *Echinacea* are more compact than plants of 'Mistral'.
2. Inflorescences of plants of the new *Echinacea* have about four whorls of ray florets whereas inflorescences of plants of 'Mistral' have a single whorl of ray florets.
3. Ray florets of plants of the new *Echinacea* are darker reddish purple in color than ray florets of plants of 'Mistral'.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSSWFU' grown in a container.

Figure 2:
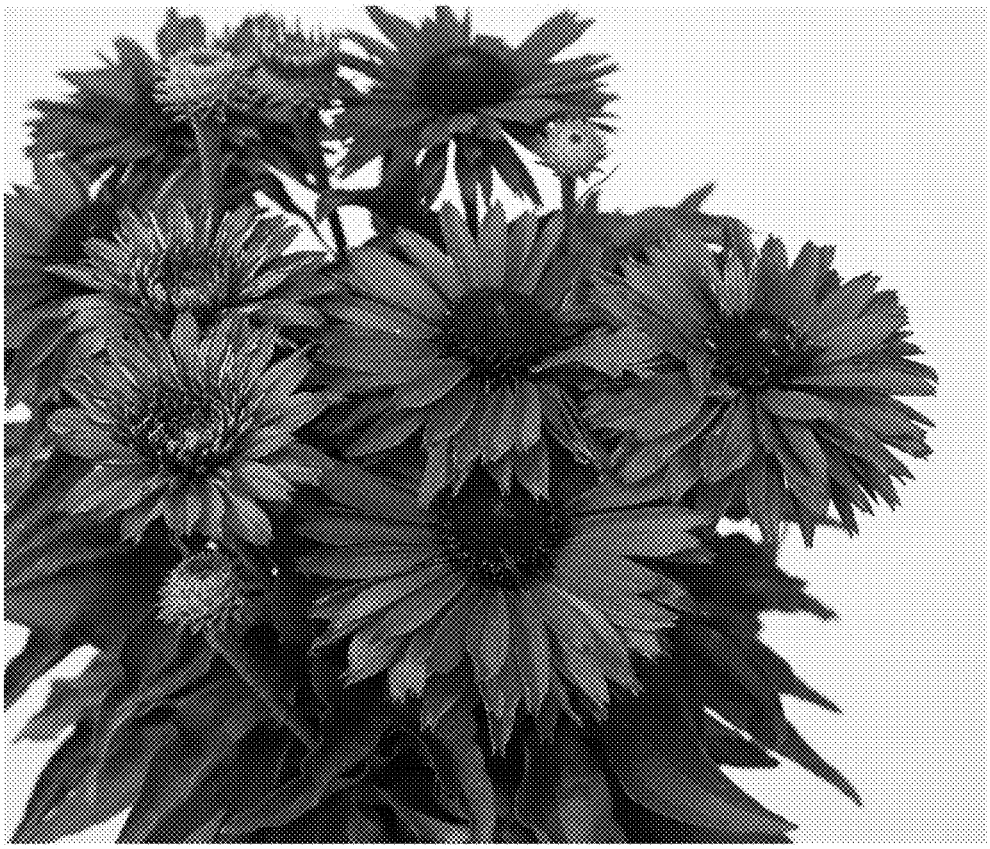

The photograph at the top of the second sheet (FIG. 2) is a close-up view of typical inflorescences of 'IFECSSSWFU'.

Figure 3:
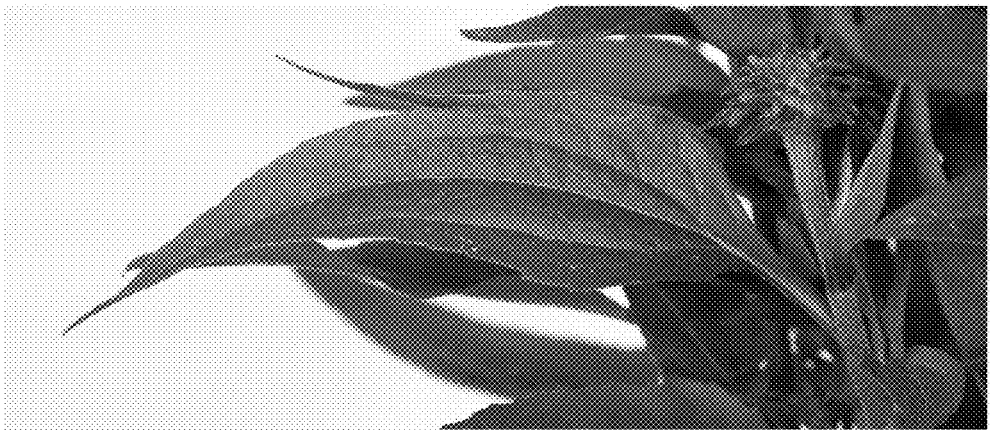

The photograph at the bottom of the second sheet (FIG. 3) is a close-up view of typical leaves of 'IFECSSSWFU'.

DETAILED BOTANICAL DESCRIPTION

The aforementioned photographs and following observations and measurements describe plants grown during the summer in 19-cm containers in an outdoor nursery in Heerhugowaard, The Netherlands and under cultural practices typically used in commercial *Echinacea* production. During the production of the plants, day temperatures ranged from 18C to 34C and night temperatures ranged from 8C to 18C. Plants were 15 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSSWFU'.

Parentage:

*Female parent.*—Proprietary selection of *Echinacea hybrida* identified as code number 009-15-K009-01, not patented.

*Male parent.*—Proprietary selection of *Echinacea hybrida* identified as code number 009-16-K042-02, not patented.

Propagation:

*Type.*—By in vitro meristem culture.

*Time to initiate roots, summer.*—About twelve days at temperatures about 20C.

*Time to initiate roots, winter.*—About 16 days at temperatures about 20C.

*Time to produce a rooted young plant, summer.*—About 36 days at temperatures about 18C.

*Time to produce a rooted young plant, winter.*—About 42 days at temperatures about 18C.

*Root description.*—Thick, fleshy; typically white in color, actual color of the roots is dependent on substrate composition, water quality, fertilizer type and formulation, substrate temperature and physiological age of roots.

*Rooting habit.*—Moderately freely branching; sparse.

Plant description:

*Plant form and growth habit.*—Herbaceous perennial; relatively compact and broadly upright plant habit; obovate to flattened globular in overall shape; freely basal branching habit with about eleven primary lateral branches and about 14 secondary lateral branches developing per plant; moderately vigorous to vigorous growth habit and moderate growth rate.

*Plant height.*—About 33.8 cm.

*Plant diameter or spread.*—About 37.8 cm.

*Lateral branches.*—Length: About 10.2 cm. Diameter: About 6 mm. Internode length: About 2.1 cm. Aspect: Erect to about 20 degrees from vertical. Strength: Strong. Texture: Moderately to densely pubescent; strigose. Color: Close to a blend of 144A and 146B; lower leaf nodes, tinged with close to 186B and 186C.

Leaf description:

*Basal and cauline leaves.*—Arrangement: Alternate, simple. Length: About 10.3 cm. Width: About 4.1 cm. Shape: Ovate. Apex: Narrowly acute. Base: Short attenuate. Margin: Mostly entire; occasionally, sparse and irregular shallow indentations; moderately undulate. Texture and luster, upper surface: Moderately to densely pubescent, strigose and rough; matte. Texture and luster, lower surface: Moderately to densely pubescent, strigose and rough; slightly glossy. Venation pattern: Pinnate. Color: Developing leaves, upper surface: Close to a blend of 143A and 146A. Developing leaves, lower surface: Close to 146A. Fully expanded leaves, upper surface: Close to NN137A; venation, close to 144B. Fully expanded leaves, lower surface: Close to a blend of 137B and 147B; venation, close to 146C.

*Petioles, basal and cauline leaves.*—Length: About 2.8 cm. Diameter: About 2.5 mm by 4.5 mm. Texture, upper surface: Smooth, glabrous. Texture, lower surface: Sparsely pubescent. Color, upper surface: Close to 137B; midvein, close to 146C to 146D and variably tinged with close to 178A. Color, lower surface: Close to NN137D; midvein, close to 144A.

Inflorescence description:

*Appearance.*—Semi-double type inflorescences with ray and disc florets arranged on a capitulum; inflorescences positioned upright above the foliar plane on mostly upright and strong peduncles.

*Flowering habit.*—Freely flowering habit with about 25 developing and fully developed inflorescences per plant.

*Fragrance.*—Faintly fragrant; sweet and pleasant.

*Time to flower.*—Plants flower continuously from late June into late September in The Netherlands.

*Inflorescence longevity.*—Inflorescences maintain good substance for about three weeks on the plant; inflorescences persistent.

*Inflorescence buds.*—Height: About 2.8 cm. Diameter: About 3.6 cm. Shape: Broadly obovate with a flattened top. Color: Immature involucral bracts, close to 138A and 138B; immature ray florets, close to 185C with apices, close to 144C; immature receptacle spines, close to 146A.

*Inflorescence size.*—Diameter: About 11.8 cm. Depth (height): About 5.1 cm. Disc diameter: About 3.8 cm.

*Receptacles.*—Height: About 1.1 cm. Diameter: About 1.7 cm. Shape: Broadly ovate to close to deltoid. Color: Close to 155B and 157A.

*Ray florets.*—Quantity and arrangement: About 74 to 108 arranged in about four whorls at the base of the receptacle. Length: About 5 cm. Width: About 1.25 cm. Shape: Oblanceolate; slightly carinate. Apex: Emarginate to praemorse. Base: Cuneate. Margin: Entire. Texture and luster, upper surface: Smooth, glabrous; moderately velvety; matte. Texture and luster, lower surface: Smooth, glabrous; slightly glossy. Aspect: About 35 degrees from horizontal; with development, apices curled slightly downward. Color: When opening, upper surface: Close to 47A and 47B. When opening, lower surface: Close to 186A and 186B. Fully opened, upper surface: Close to 61B, 64B and a blend of 61B and 64B; venation, close to a blend of 61B and 64B; color becoming closer to 186B and proximally, close to N186D, with subsequent development. Fully opened, lower surface: Close to 60B and 60C and proximally, close to 186B and 186C; venation, similar to lamina color; color becoming closer to 186A and 186B with subsequent development.

*Disc florets.*—Quantity and arrangement: About 360 per inflorescence, arranged spirally at the center of the inflorescence. Length: About 1.2 cm. Diameter: About 3.25 mm. Shape: Tubular; proximal 10% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 144A tinged with close to N186C. Mid-section: Close to 145C. Base: Close to 183A. Color, fully opened, inner and outer surfaces: Apex: Close to 178B. Mid-section: Close to 152D. Base: Close to N186C.

*Receptacle spines.*—Quantity: One per disc floret; about 360 per inflorescence. Shape: Acicular. Apex: Acute. Base: Attenuate. Texture and luster: Smooth, glabrous; glossy. Color: Apex: Close to 187A. Mid-section: Close to 20A. Base: Close to 144B.

*Involucral bracts.*—Quantity per inflorescence: About 100 arranged in about four whorls. Length: About 1 cm. Width: About 3 mm. Shape: Narrowly ovate; close to horizontal to slightly reflexed. Apex: Acute. Base: Cuneate. Margin: Entire. Texture and luster, upper and lower surfaces: Moderately pubescent; margins, moderately pubescent; slightly glossy. Color, upper and lower surfaces: Close to 137C; towards the margins, close to 137A.

*Peduncles.*—Length: About 12 cm. Diameter: About 5.5 cm. Strength: Strong. Aspect: Mostly upright. Texture: Moderately pubescent; strigose. Color: Close to 144B with blotches, close to 146B.

*Reproductive organs.*—Androecium (present on ray and disc florets): Quantity per floret: Five. Filament length: About 4 mm. Filament color: Close to 150D. Anther length: About 4 mm. Anther shape: Linear. Anther color: Close to 200A. Pollen amount: Moderate. Pollen color: Close to 17B. Gynoecium (present only on disc florets): Quantity per floret: One. Pistil length: About 8 mm. Stigma shape: Decurrent, unequal. Stigma color: Close to 200A. Style length: About 6.5 mm. Style color: Close to 150D. Ovary color: Close to 157C. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35C and to be hardy to USDA Hardiness Zones 3 to 4.

It is claimed:

1. A new and distinct *Echinacea* plant named 'IFECSSS-WFU' as illustrated and described.

* * * * *